US012357150B2

(12) United States Patent
Pereira et al.

(10) Patent No.: US 12,357,150 B2
(45) Date of Patent: Jul. 15, 2025

(54) STONE IDENTIFICATION METHODS AND SYSTEMS

(71) Applicant: Boston Scientific Scimed, Inc., Maple Grove, MN (US)

(72) Inventors: Peter J. Pereira, Mendon, MA (US); Michael S. H. Chu, Brookline, MA (US); Elizabeth Stokley, Baltimore, MD (US); David Salto, Hopedale, MA (US); Candace Rhodes, Walpole, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/584,788

(22) Filed: Feb. 22, 2024

(65) Prior Publication Data

US 2024/0188792 A1   Jun. 13, 2024

Related U.S. Application Data

(63) Continuation of application No. 17/574,598, filed on Jan. 13, 2022, now Pat. No. 11,937,768, which is a
(Continued)

(51) Int. Cl.
*G06K 9/00* (2022.01)
*A61B 1/00* (2006.01)
(Continued)

(52) U.S. Cl.
CPC ........ *A61B 1/00009* (2013.01); *A61B 1/0005* (2013.01); *A61B 1/018* (2013.01);
(Continued)

(58) Field of Classification Search
CPC .. A61B 5/201; A61B 1/00; G06K 9/00; G06T 7/62
(Continued)

(56) References Cited

U.S. PATENT DOCUMENTS

| 8,535,250 B2 | 9/2013 | Owen et al. |
| 9,696,897 B2 * | 7/2017 | Garcia ...................... G06T 7/62 |

(Continued)

FOREIGN PATENT DOCUMENTS

| CN | 2936128 Y | 8/2007 |
| CN | 105682535 A | 6/2016 |

(Continued)

OTHER PUBLICATIONS

International Search Report and Written Opinion for International Application No. PCT/US2018/012017, dated Apr. 28, 2018 (16 pages).

(Continued)

*Primary Examiner* — Seyed H Azarian
(74) *Attorney, Agent, or Firm* — Seager, Tufte & Wickhem, LLP

(57) ABSTRACT

Aspects of stone identification methods and systems are described. According to one aspect, an exemplary method comprises: transmitting to a processing unit, with an imaging element mounted on a distal end of a scope, image data about a stone object inside a body cavity; generating from the image data, with the processing unit, a visual representation of the stone object and the body cavity; establishing from a user input, with the processing unit, a scale for the visual representation; determining from the visual representation, with the processing unit, a size of the stone object on the scale; comparing, with the processing unit, the size of the stone object with a predetermined maximum size to determine a removal status; and augmenting, with the processing unit, the visual representation to include an indicator responsive to the removal status. Associated systems are also described.

20 Claims, 8 Drawing Sheets

Related U.S. Application Data continuation of application No. 16/842,091, filed on Apr. 7, 2020, now Pat. No. 11,253,220, which is a continuation of application No. 16/445,678, filed on Jun. 19, 2019, now Pat. No. 10,646,187, which is a continuation of application No. 15/859,797, filed on Jan. 2, 2018, now Pat. No. 10,368,820.

(60) Provisional application No. 62/443,320, filed on Jan. 6, 2017.

(51) Int. Cl.

| | | |
|---|---|---|
| *A61B 1/018* | (2006.01) | |
| *A61B 1/307* | (2006.01) | |
| *A61B 5/107* | (2006.01) | |
| *A61B 5/20* | (2006.01) | |
| *A61B 6/00* | (2006.01) | |
| *A61B 8/00* | (2006.01) | |
| *A61B 8/08* | (2006.01) | |
| *A61B 8/12* | (2006.01) | |
| *A61B 17/225* | (2006.01) | |
| *A61B 18/26* | (2006.01) | |
| *A61B 34/00* | (2016.01) | |
| *G06F 3/0484* | (2022.01) | |
| *G06F 3/0488* | (2022.01) | |
| *G06T 11/60* | (2006.01) | |
| *A61B 18/00* | (2006.01) | |
| *A61B 34/20* | (2016.01) | |
| *A61B 90/00* | (2016.01) | |
| *A61N 5/06* | (2006.01) | |

(52) U.S. Cl.
CPC ............ *A61B 1/307* (2013.01); *A61B 5/1076* (2013.01); *A61B 5/20* (2013.01); *A61B 6/5217* (2013.01); *A61B 8/0841* (2013.01); *A61B 8/085* (2013.01); *A61B 8/12* (2013.01); *A61B 8/4254* (2013.01); *A61B 17/2256* (2013.01); *A61B 18/26* (2013.01); *A61B 34/25* (2016.02); *G06F 3/0484* (2013.01); *G06F 3/0488* (2013.01); *G06T 11/60* (2013.01); *A61B 1/00048* (2013.01); *A61B 17/2255* (2013.01); *A61B 2018/00505* (2013.01); *A61B 2018/00517* (2013.01); *A61B 2018/00982* (2013.01); *A61B 2034/2074* (2016.02); *A61B 2090/061* (2016.02); *A61N 2005/061* (2013.01)

(58) Field of Classification Search
USPC ....... 382/100, 103, 106, 128–132, 154, 162, 382/168, 173, 180–181, 189, 199, 209, 382/220, 232, 254, 275–276, 286–291, 382/305, 321; 600/103, 160; 606/127, 606/128

See application file for complete search history.

(56) References Cited

U.S. PATENT DOCUMENTS

| | | | |
|---|---|---|---|
| 2009/0299187 A1 | 12/2009 | Bailey et al. | |
| 2011/0245841 A1* | 10/2011 | Shohat | A61B 17/221 606/127 |
| 2012/0316396 A1* | 12/2012 | Robertson | A61B 1/00009 600/160 |
| 2015/0289937 A1 | 10/2015 | Chia et al. | |
| 2015/0313444 A1 | 11/2015 | Wolf | |
| 2015/0320383 A1 | 11/2015 | Dunmire et al. | |
| 2015/0366571 A1* | 12/2015 | Navve | A61B 5/201 606/128 |
| 2016/0051125 A1* | 2/2016 | Wolf | A61B 18/26 600/103 |
| 2016/0135894 A1 | 5/2016 | Finkman et al. | |
| 2016/0199079 A1* | 7/2016 | Chu | A61B 17/221 606/127 |
| 2017/0220754 A1* | 8/2017 | Harrah | A61B 18/26 |
| 2018/0221039 A1* | 8/2018 | Shah | A61B 1/307 |

FOREIGN PATENT DOCUMENTS

| | | |
|---|---|---|
| DE | 102005031124 B4 | 3/2012 |
| WO | 2015175151 A1 | 11/2015 |
| WO | 2017132365 A1 | 8/2017 |

OTHER PUBLICATIONS

Chinese Office Action in Chinese Application No. 201880006040.3, dated Apr. 28, 2021. (10 pages).

Japanese Office Action in Japanese Application No. 2019-536300, dated Oct. 12, 2021 (2 pages).

* cited by examiner

STONE IDENTIFICATION METHODS AND SYSTEMS

CROSS-REFERENCE TO RELATED APPLICATIONS

This application is a continuation of U.S. application Ser. No. 17/574,598, filed Jan. 13, 2022, which is a continuation of U.S. application Ser. No. 16/842,091, filed Apr. 7, 2020, which is a continuation of U.S. application Ser. No. 16/445,678, filed Jun. 19, 2019, now U.S. Pat. No. 10,646,187, which is a continuation of U.S. application Ser. No. 15/859,797, filed Jan. 2, 2018, now U.S. Pat. No. 10,368,820, which claims the benefit of priority to U.S. Provisional Application No. 62/443,320, filed Jan. 6, 2017, all of which are incorporated by reference in their entireties

TECHNICAL FIELD

Aspects of the present disclosure generally relate to medical devices and procedures. Particular aspects relate to stone identification methods and systems.

BACKGROUND

Lithotripsy for urinary stones may be carried out intracorporeally using a lithotripsy device including a flexible or rigid ureteroscope configured to fragment each stone and remove the fragments. Laser energy is conventionally used to fragment the stones, although other energies may be used, including those applied by ballistic, ultrasonic, and/or electrohydraulic means. Stone fragmentation is a desirable effect. With many lithotripsy devices, however, the size of each stone fragment cannot be controlled. For example, in response to laser energy, a stone may be broken into a plurality of stone fragments, each having unpredictably different sizes. Fragment size may determine the length of treatment time. For example, larger stones must be removed or further fragmented, else they will most likely grow back into even larger stones.

Accurately measuring stone size is a known problem. Many purported solutions require the surgeon to estimate stone size from an image, such as an X-ray image. These estimations may be inaccurate, especially if the image is of low resolution or visibility. Because of these inaccuracies, the surgeon may remove and/or fragment more stones than otherwise required, or engage in an arduous removal process. Both options are time consuming. For example, time may be lost if the surgeon introduces a retrieval device based on an estimated stone size, then finds the fragment too big, requiring removal of the retrieval device, further fragmentation of the stone, and eventual re-introduction of the retrieval device. Aspects of the methods and systems described herein address these problems and other deficiencies of the prior art.

SUMMARY

Aspects of the present disclosure relate to stone identification methods and systems. Numerous aspects are now described.

One aspect is a method. The method may comprise: transmitting to a processing unit, with an imaging element mounted on a distal end of a scope, image data about a stone object inside a body cavity; generating from the image data, with the processing unit, a visual representation of the stone object and the body cavity; establishing, with the processing unit, a scale for the visual representation; determining from the visual representation, with the processing unit, a size of the stone object on the scale; comparing, with the processing unit, the size of the stone object with a predetermined maximum size to determine a removal status; and augmenting, with the processing unit, the visual representation to include an indicator responsive to the removal status.

According this aspect, transmitting to the processing unit may include positioning the distal end of the scope at a first position relative to the stone object, and the method may further comprise: moving the distal end of the scope to a second position relative to the stone object; positioning the imaging element adjacent the stone object; and capturing the image data with the imaging element at the second position. Generating the visual representation may comprise transmitting at least a portion of the image data to an interface device. For example, the interface device may be a touchscreen display. Establishing the scale may comprise: positioning a reference element adjacent the stone object; comparing one or more markers on the reference element to the stone object to determine a reference measurement; and defining the scale based on the reference measurement. The reference element may be an optical fiber movably disposed in lumen of the scope, the markers may comprise one or more tick marks located on a distal portion of the optical fiber. Positioning the reference element may comprise: moving the optical fiber distally within the lumen until the distal portion of the optical fiber is located inside the body cavity; and positioning the one or more tick marks adjacent the stone object.

In some aspects, determining the size of the stone object may comprise: establishing, with the interface device, a first reference point and a second reference point on the visual representation of the stone object; calculating, with the processing unit, a reference measurement between the first and second reference points; and determining from the reference measurement, with the processing unit, the size of the stone object with the scale. For example, the interface device may be a touchscreen display, and the first and second reference points may be established by touching various points on the display. In other aspects, determining the size of the stone object may comprise: obtaining from the image data, with an image analyzer, a reference measurement the stone object within a first image frame included within the image data; and determining from the reference measurement, with the processing unit, a two-dimensional size of the stone object in the first image frame. The reference measurement may include a plurality of reference measurements, determining the size of the stone object may comprise: determining from the plurality of reference measurements, with the processing unit, a cross-sectional area of the stone object within the imaging plane. In some aspects, the method may further comprise moving the imaging element or the stone object to determine a depth of the stone object, and determining from the cross-sectional area and depth, with the processing unit, a volume of the stone object.

In other aspects, the distal end of the scope may comprise a wave energy transducer, and determining the size of the stone object may comprise: directing, with the processing unit, a wave energy from the wave energy transducer toward the stone object; receiving, with the transducer, a reflected portion of the wave energy; defining from the reflected portion of the wave energy, with the processing unit, a depth of the stone object; and determining from the cross-sectional area and depth, with the processing unit, a volume of the stone object. Determining the size may comprise: determining from the plurality of reference measurements, with the processing unit, a surface area of the stone object, and/or determining from the reflected portion of the wave energy, with the processing unit, a density of the stone object.

Comparing the size of the stone object may comprise: determining a first removal status when the size of the stone object is greater than the predetermined maximum size; and determining a second removal status when the size of the stone object is less than the predetermined maximum size. According to these aspects, augmenting the visual representation may comprise overlaying either a first indicator onto the visual representation based on the first removal status, or a second indicator onto the visual representation based on the second removal status. The method also may comprise augmenting, with the processing unit, the visual representation to include an indicator responsive to at least one of the cross-sectional area of the object, the volume of the object, the surface area of the object, or the density of the object.

Another aspect of the present disclosure is a method comprising: obtaining, with an imaging element, image data about a plurality of stone objects in a body cavity; generating from the imaging data, with the processing unit, a visual representation of the plurality of stone objects in the body cavity; determining from the visual representation, with the processing unit, physical characteristics of the plurality of stone objects; analyzing, with the processing unit, the physical characteristics to determine a removal status for each of the plurality of stone objects; and augmenting, with the processing unit, the visual representation responsive to each removal statuses.

According to this aspect, the physical characteristics may comprise a size of each of the plurality of stone objects, and determining the physical characteristics may comprise: establishing, with the processing unit, a scale of the image data; analyzing, with an image analyzer, the imaging data to obtain reference measurements of each of the plurality of stone objects; and determining from the reference measurements, with the processing unit, the size of each of the plurality of stone objects. Some exemplary methods may comprise augmenting, with the processing unit, the visual representation to include an indicator responsive to the size of each of the plurality of stone objects. These methods may comprise: performing a treatment on one of the stone objects; and repeating the obtaining, generating, determining, and augmenting steps.

Yet another aspect of the present disclosure is a method comprising: obtaining, with an imaging element, image data about one or more stone objects inside of a kidney; generating from the image data, with a processing unit, a visual representation of the one or more stone objects in the kidney; determining, with the processing unit, from the visual representation, a stone width each of the one or more stone objects; comparing, with the processing unit, each stone width with a predetermined maximum width to determine removal status for each of the one or more stone objects; and augmenting, with the processing unit, the visual representation to include an indicator of the removal status of each of the one or more stones.

It may be understood that both the foregoing summary and the following detailed descriptions are exemplary and explanatory only, neither being restrictive of the inventions claimed below.

BRIEF DESCRIPTION OF THE DRAWINGS

The accompanying drawings are incorporated in and constitute a part of this specification. These drawings illustrate aspects of the present disclosure that, together with the written descriptions herein, serve to explain this disclosure. Each drawing depicts one or more exemplary aspects according to this disclosure, as follows.

DETAILED DESCRIPTION

Figure 1A:
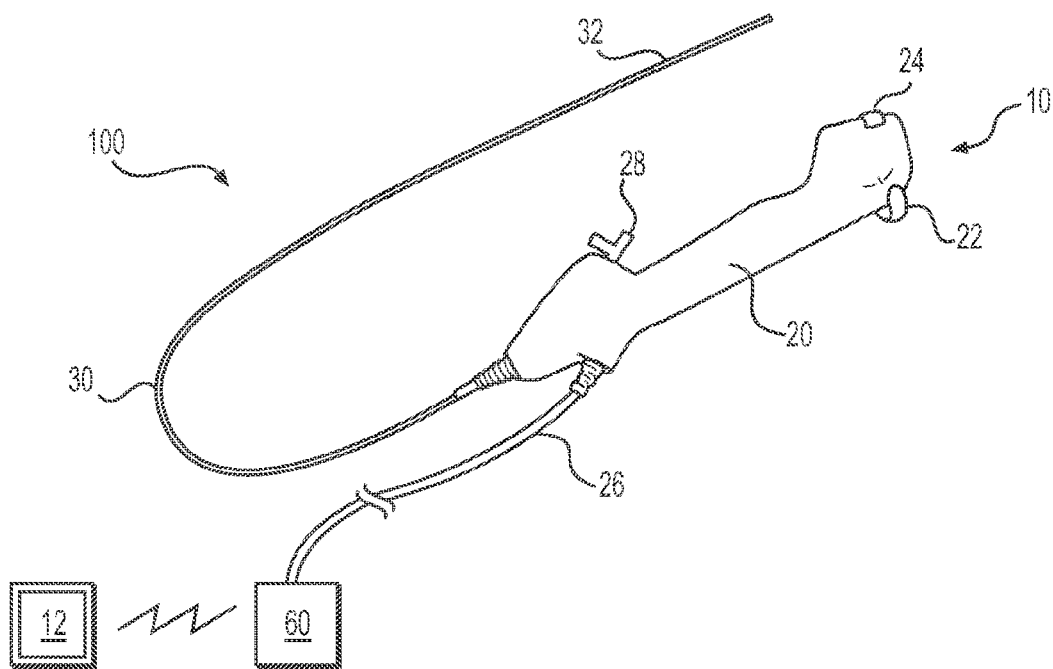
FIGS. 1A-D depict aspects of an exemplary system including a scope operable with a processing unit to generate image data.

Aspects of the present disclosure are now described with reference to exemplary stone identification methods and systems. Some aspects are described with reference to medical procedures where a scope is guided through a body until a distal end of the scope is located in a body cavity including one or more stone objects. For example, the scope may include an elongated sheath that is guided through a urethra, a bladder, and a ureter until a distal end of the sheath is located in a calyx of a kidney, adjacent one or more kidney stones. References to a particular type of procedure, such as medical; body cavity, such as a calyx; and stone object, such as a kidney stone, are provided for convenience and not intended to limit the present disclosure unless claimed. Accordingly, the concepts described herein may be utilized for any analogous device or method—medical or otherwise, kidney-specific or not.

Numerous axes are described. Each axis may be transverse, or even perpendicular, with the next so as to establish a Cartesian coordinate system with an origin point O. One axis may extend along a longitudinal axis of an element or body path. The directional terms "proximal" and "distal," and their respective initials "P" and "D," may be utilized to describe relative components and features in relation to these axes. Proximal refers to a position closer to the exterior of the body or a user, whereas distal refers to a position closer to the interior of the body or further away from the user. Appending the initials "P" or "D" to an element number signifies a proximal or distal location. Unless claimed, these terms are provided for convenience and not intended to limit the present disclosure to a particular location, direction, or orientation.

As used herein, the terms "comprises," "comprising," or like variation, are intended to cover a non-exclusive inclusion, such that a device or method that comprises a list of elements does not include only those elements, but may include other elements not expressly listed or inherent thereto. Unless stated otherwise, the term "exemplary" is used in the sense of "example" rather than "ideal." Conversely, the terms "consists of" and "consisting of" are intended to cover an exclusive inclusion, such that a device or method that consists of a list of elements includes only those elements.

An exemplary system 100 now described with reference to FIGS. 1A-D, 2, 3A-D, and 4 as comprising a scope 10 operable with a processing unit 60 to determine characteristics of a stone object 5 in a body cavity 3.

Figure 1B:
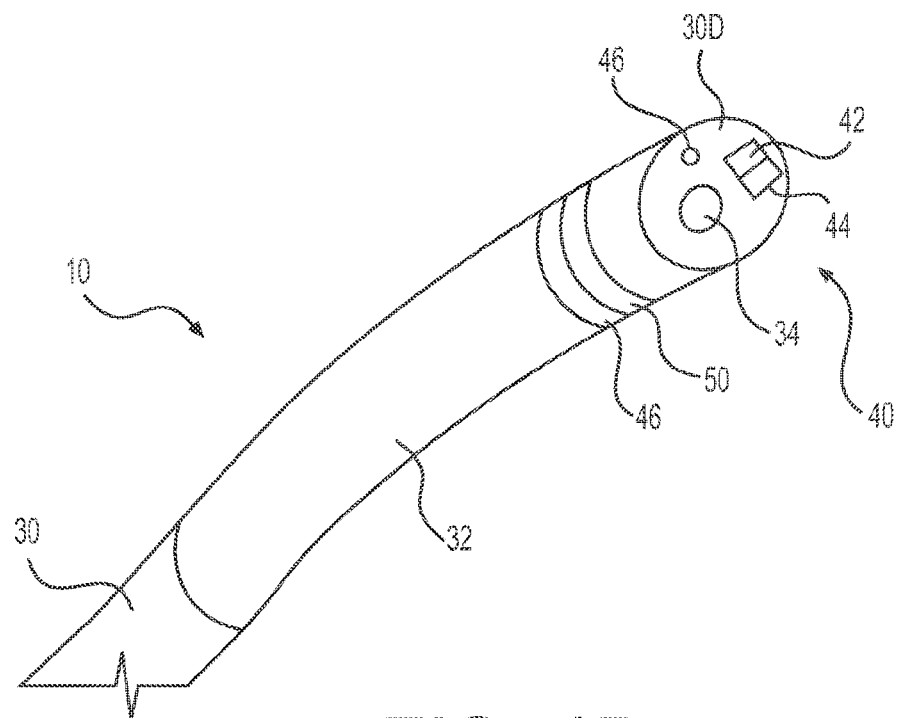

Scope 10 of FIGS. 1A-D, for example, may be a modified single-use digital ureteroscope similar to those sold by Boston Scientific Scimed, Inc., under the brand name Lithovue®. In this example, scope 10 comprises: a handle 20 with a first actuator 22 and a second actuator 24; a power and signal cord 26; a port 28; and an elongated sheath 30 with a steerable portion 32. As shown in FIG. 1B, sheath 30 comprises a working channel 34, and an imaging element 40 configured to generate image data. An exemplary processing unit 60 is depicted in FIG. 2. As described below, processing unit 60 may be configured to generate a visual representation 80 from the image data, transmit the visual representation 80 to one or more interface devices 12 (e.g., a touchscreen display), and/or augment the representation 80.

Figure 1C:
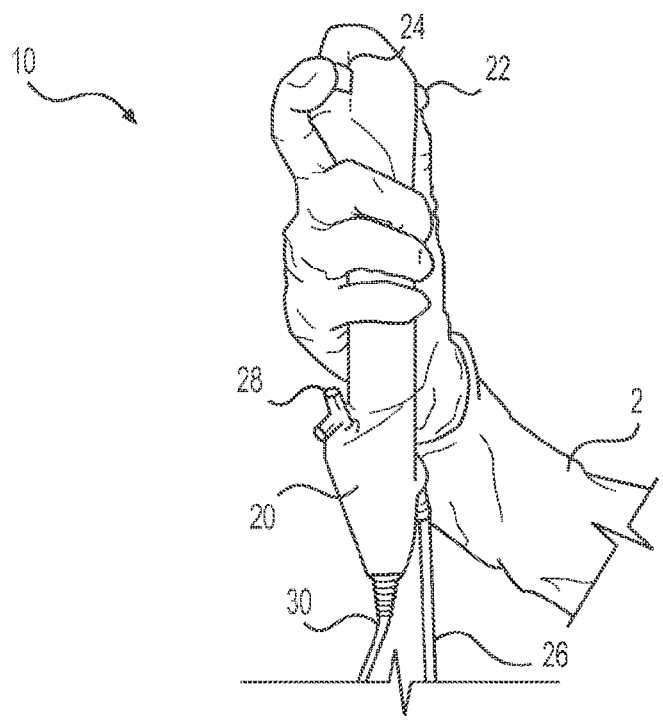
Figure 2:
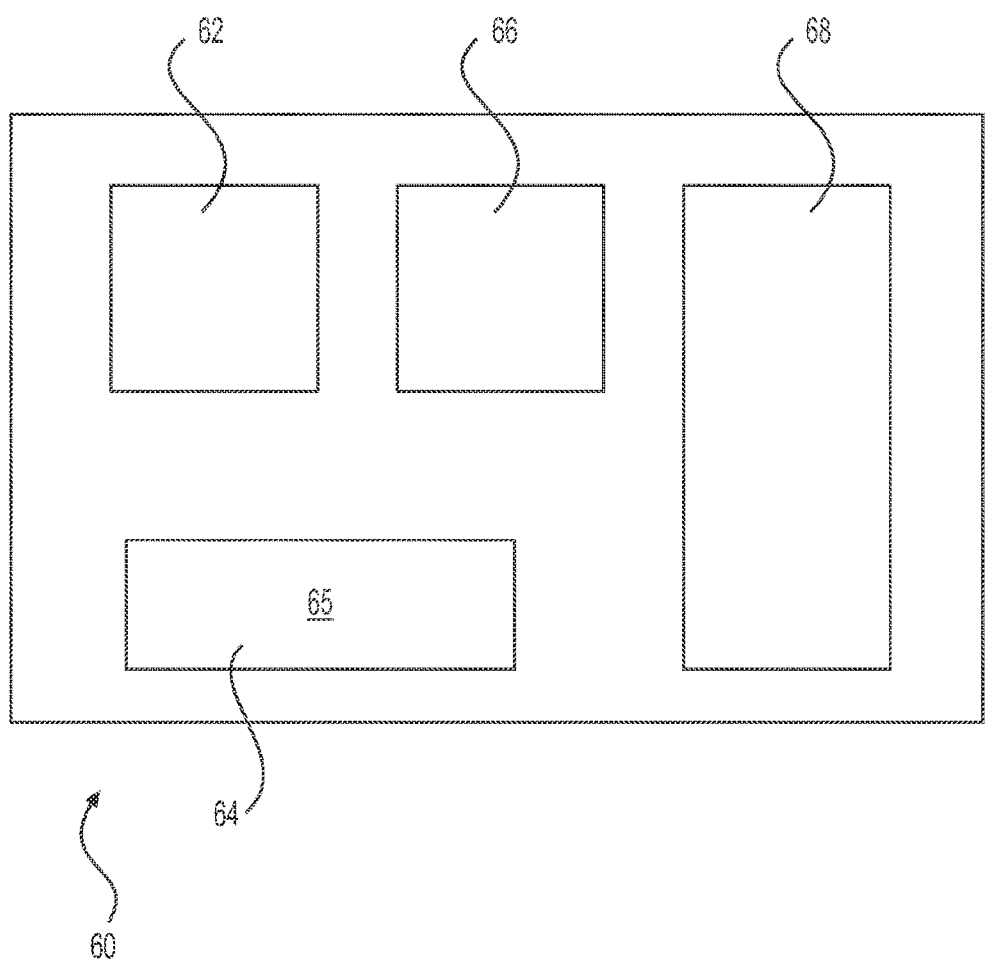
FIG. 2 depicts an exemplary processing unit.

As shown in FIGS. 1A and 1C, handle 20 of scope 10 may be positioned in a hand of a user 2 so that first actuator 22 is operable by a thumb on the hand of user 2, and second actuator 24 is operable by a finger on the same hand. First actuator 22 may be operable to articulate steerable portion 32 by application of forces to the pull-wires contained within sheath 30, and second actuator 24 may be operable with to generate and/or augment visual representation 80 by sending commands to processing unit 60. As described below, system 100 may have a manual mode, wherein imaging data is generated each time user 2 depresses second actuator 24; and an automatic mode, wherein the imaging data is generated automatically by processing unit 60. Although depicted as part of handle 20, second actuator 24 may be located anywhere in system 100, and need not be a physical element. For example, second actuator 24 may be a touch-sensitive icon displayed on the one or more interface devices 12.

Power and signal cord 26 is depicted in FIGS. 1A and 1C as a wire (e.g., an electrical wire) as being configured to transmit imaging data to processing unit 60. Any wired or wireless transmission technology may be used. For example, cord 26 may alternatively be a wireless communication device (e.g., an radio transceiver), and scope 10 may include an alternate power source (e.g., a battery).

Figure 1D:
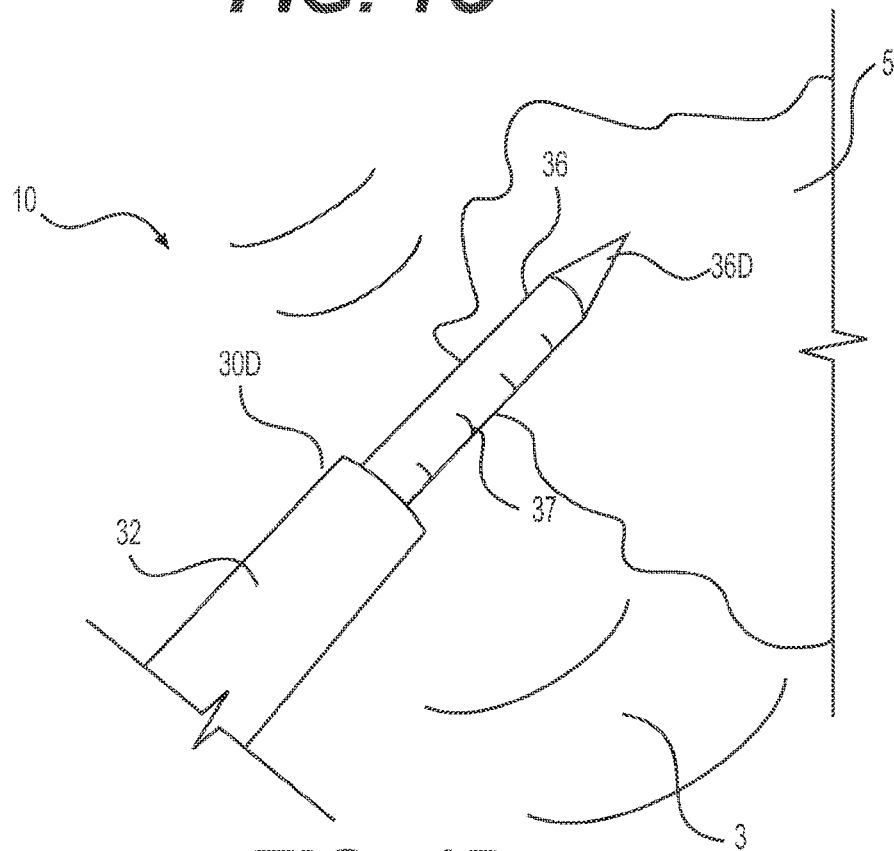

As shown in FIG. 1A, port 28 may be mounted on a distal portion of handle 20, and include openings in communication with working channel 34. An elongated tool may be inserted through port 28, and moved distally through the distal portion of handle 20 and/or working channel 34. The elongated tool may be used to treat and/or move stone object 5. In FIG. 1D, for example, an optical fiber 36 has been inserted through port 28, handle 20, and working channel 34 until a distal end 36D of the fiber 36 is located in body cavity 3 and/or adjacent stone object 5. As shown, distal end 36D may be configured to move stone object 5, and/or include a distal portion including one or more markers 37, depicted in FIG. 1D as a plurality of tick marks. As described further below, a size of each stone object 5 may be determined from a known distance between each marker 37. Each marker 37 may comprise any visual marking, arrangement, or shape, including bar codes, QR codes, and the like.

In FIGS. 1A-B, elongated sheath 30 extends distally from handle 20 before terminating at distal end 30D of sheath 30. Steerable portion 32 is located adjacent distal end 30D. Working channel 34 extends from port 28, through steerable portion 32, and out of the distal end 30D of sheath 30. In FIG. 1B, a single working channel 34 extends through a distal-facing surface of distal end 30D. Any number of channels 34 may be provided, opening in any direction, including any direction that accommodates an end-fire or side-fire configuration for optical fiber 36.

Imaging element 40 is mounted on distal end 30D of sheath 30, and operable to generate image data. Imaging element 40 may include any imaging technology. In FIG. 1B, for example, imaging element 40 includes a digital camera circuit 42 and a light emitting diode 44 that are operable with processing unit 60 to generate a video feed of body cavity 3 and/or stone object 5. The video feed may include a plurality of image frames captured by imaging element 40 at one or more frame rates, spectrums, and/or positions within body cavity 3. Various image frames are described herein, including first and second image frames, each frame being included within the video feed.

As shown in FIG. 1B, imaging element 40 may be fixedly mounted on distal end 30D and moved by operating steerable portion 32 of elongated sheath 30 with first actuator 22. Imaging element 40 may be moved in body cavity 3 and/or relative to a stone object 5 while the video feed is being generated so that the depiction of object 5 in each image frame is slightly different. For example, element 40 may be moved to generate a video feed including at least one first image frame defined by a first axis extending through stone object 5, and one or more second image frames defined by a second axes extending through stone object 5, wherein the first axis is transverse with the second axis. As described below, processing unit 60 is configured to determine characteristics of the object 5 from the first and second image frames, track those characteristics frame to frame, and make additional determinations therefrom.

An exemplary processing unit 60 is depicted in FIG. 2 as including one or more microcontrollers 62, a memory 64 including computer-readable instructions 65, a Transceiver 68, and an image analyzer 66. Each of these elements may be assembled together within a compartment of handle 20, or located remotely therefrom (e.g., in one more locations). The one more microcontrollers 62, for example, may be located in handle 20 and/or distributed through system 100. Memory 64 may include any machine-readable storage medium. Computer-readable instructions 65 may be stored in memory 64 and executed by the one or more microcontrollers 62 to perform aspects of the functions and/or methods described herein.

Image analyzer 66 of FIG. 2 may include any technology configured to determine a two or three-dimensional size of stone object 5 based on image data generated by imaging element 40. For example, image analyzer 66 may be operable with one or more microcontrollers 62 to determine a two-dimensional size of stone object 5 by: receiving the video feed from imaging element 40; selecting, from the video feed, a first image frame depicting stone object 5; overlaying a measurement grid onto the first image frame; applying a scale to the measurement grid; and determining the two-dimensional size of object 5 on the grid. As described below, the scale may be manually input by user 2 or determined automatically by image analyzer 66. One or more second image frames depicting stone object 5 may be processed similarly to determine a three-dimensional size for object 5, as also described below.

Transceiver 68 may include any wired or wireless transmission means configured to place the processing unit 60 in communication with other elements of system 100 described. In FIG. 1A, for example, transceiver 68 provides wireless communication between processing unit 60 and one or more interface devices 12, allowing for generation and augmentation of visual representation 80.

Figure 5:
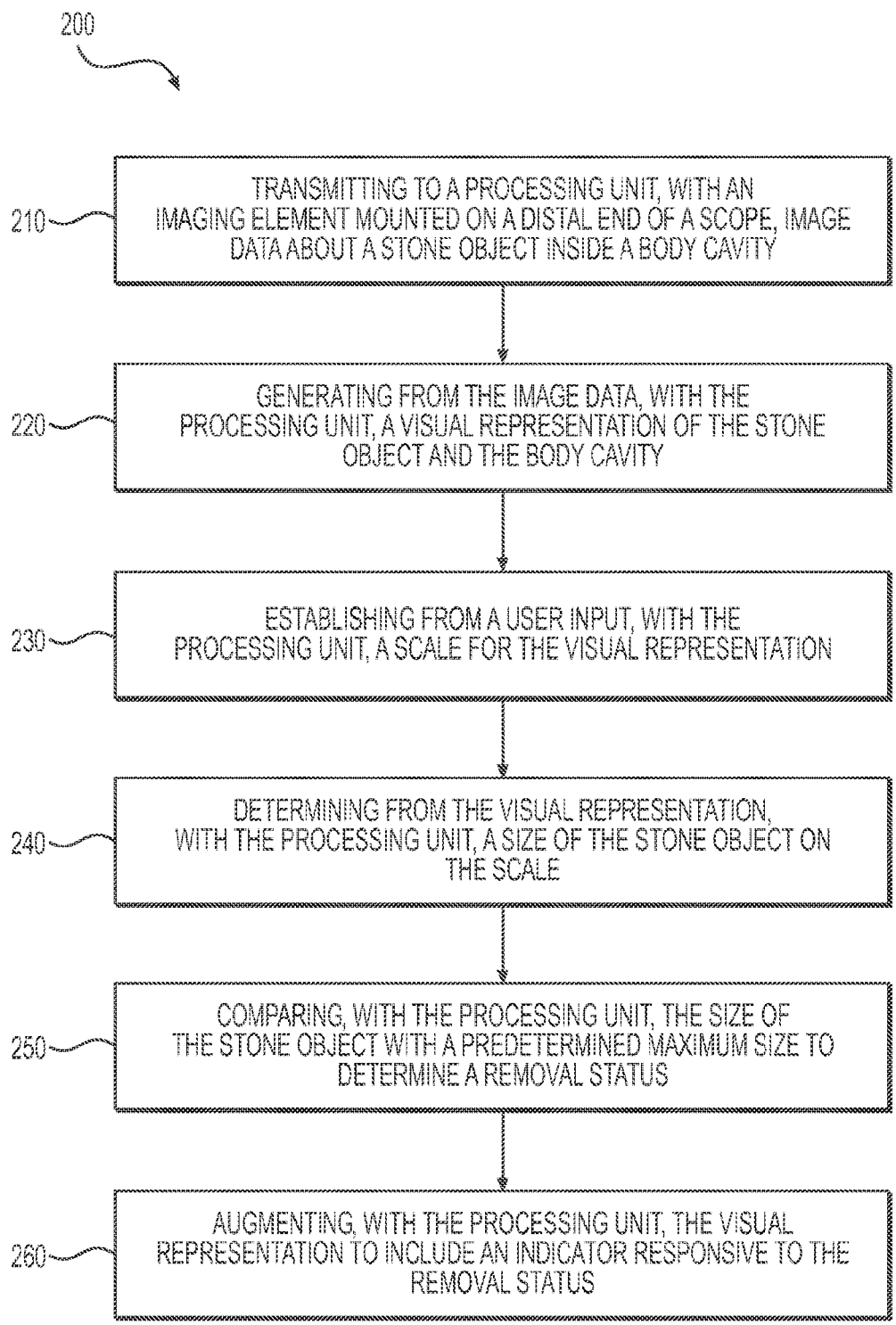
FIG. 5 depicts an exemplary method for generating and augmenting a visual representation generated from image data.
Figure 6:
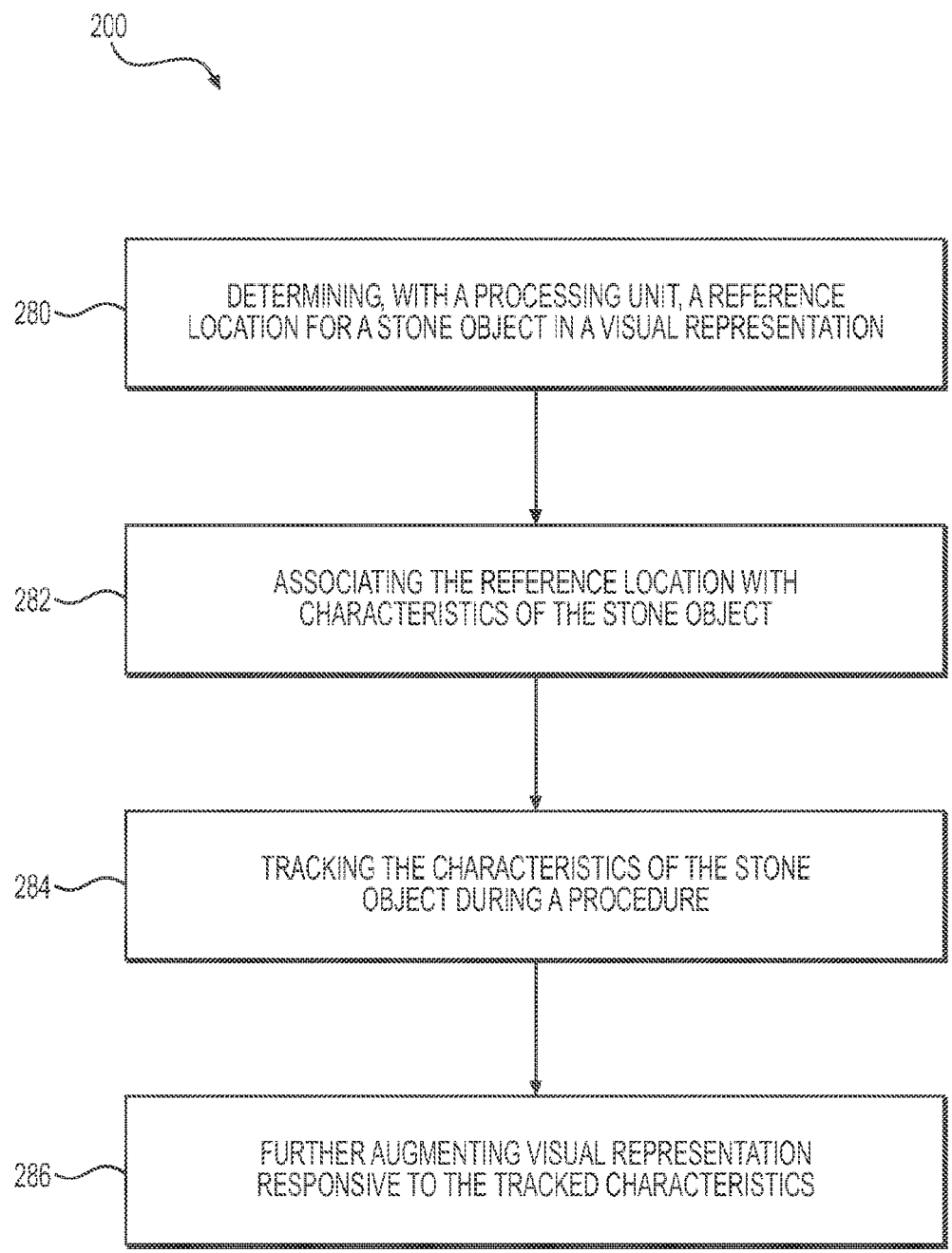
FIG. 6 depicts an exemplary method for tracking objects within a visual representation generated from image data.

Aspects of visual representation 80 are now described. One aspect is a method 200 for generating and/or augmenting representation 80 that, as shown in FIG. 5, may comprise: transmitting to processing unit 60, from imaging element 40, image data about body cavity 3 and stone object 5 (a transmitting step 210); generating from the image data, with processing unit 60, a visual representation 80 of body cavity 3 and stone object 5 (a generating step 220); establishing, with processing unit 60, a scale for visual representation 80 (an establishing step 230); determining from visual representation 80, with processing unit 60, a size of stone object 5 on the scale (a determining step 240); comparing, with processing unit 60, the size of object 5 with a predetermined maximum size to determine a removal status (a comparing step 250); and/or augmenting, with processing unit 60, the visual representation 80 to include an indicator responsive to the removal status (an augmenting step 260).

Transmitting step 210 may include any intermediate steps required to generate and transmit image data. Step 210 may include activating components of imaging element 40, such as digital camera circuit 42 and/or light emitting diode 44. For example, step 210 may comprise: generating, with imaging element 40, a video feed of stone object 5 at a predetermined frame rate; and transmitting, with cord 26, the video feed to processing unit 60. The video may be generated manually or automatically in step 210. For example, step 210 may comprise: placing system 100 in a manual mode, wherein the video feed is generated responsive to second actuator 24; or an automatic mode, wherein the feed is generated automatically responsive to targeting criteria established within memory 64. For example, in the automatic mode, image analyzer 66 may be configured to continually scan body cavity 3 and deliver an activation signal to camera circuits 42 and/or diodes 44 whenever stone object 5 has a minimum two-dimensional size, such as a minimum stone width (e.g., 2 mm).

Additional positioning steps may be performed to generate additional image data. For example, transmitting step 210 may comprise: moving imaging element 40 to a plurality of different positions about stone object 5, and generating image data at each of the different positions. Step 210 may comprise selecting one or more image frames from the video feed. For example, step 210 may comprise selecting a first image frame including stone object 5, selecting one or more second frames including the object 4, and transmitting the first and second frames to processing unit 60 along with positional data concerning the location and orientation of the first frame relative to the second frame and/or stone object 5.

Generating step 220 may comprise any intermediate step for generating visual representation 80 from image data. An exemplary visual representation 80 is depicted in FIGS. 3A-D as a two- or three-dimensional computer-generated image. As shown, visual representation 80 may comprise: an image data layer 81; and an indicator layer 83. Image data layer 81 may include the image data. For example, in step 220, visual representation 80 may be generated, with processing unit 60, by displaying image data layer 81 in a central, circular portion of interface device 12. Once generated, aspects of image data layer 81 may be combined with aspects of interface layer 83 described below (e.g., in step 260) to augment visual representation 80.

Establishing step 230 may include automatically or manually defining a scale for visual representation 80, and calibrating system 100 according thereto. In some aspects, the manufacturer may define the scale and calibrate system 100 based upon a predetermined distance between imaging element 40 and stone object 5, at which the output of image analyzer 66 comports with the actual size of object 5. For example, the predetermined distance may be proportionate to a focal length of digital camera circuit 42, allowing the actual size to be determined when circuit 42 is focused accordingly. Because the size of stone object 5 may be small (e.g., 5 mm or less), the scale may not need to be re-defined, even if the distance between imaging element 40 and stone object 5 varies slightly (e.g., +/−10%) from the predetermined distance. The calibration of system 100 may be affected prior to use (e.g., by shipping conditions). Accordingly, step 230 may comprise utilizing a reference element (e.g., a circle of known diameter) to re-define the scale and re-calibrate system 100 ex vivo, prior to use.

To accommodate a greater range of motion with body cavity 3 and/or improve the image data, the scale of visual representation 80 also may be defined and/or re-defined in vivo, during use. For example, the diameter of fiber 36 may be known, such that step 230 comprises positioning fiber 36 adjacent stone object 5 in visual representation 80; comparing the known diameter of fiber 36 with a portion of stone object 5 to determine a reference measurement; and defining the scale based on the reference measurement. As noted above, fiber 36 may include one or more markers 37, shown in FIG. 1D as a plurality of tick marks located on a distal portion 36D of fiber 36. Accordingly, step 230 may comprise: positioning the tick marks adjacent stone object 5; comparing the tick marks with a portion of stone object 5; and defining the scale from a known distance between the tick marks.

Aspects of establishing step 230 may be performed by user 2 and/or processing unit 60. For example, user 2 may perform the comparing steps, and the defining steps may comprise inputting the scale to processing unit 60 (e.g., with one or more interface devices 12). One or more markers 37 may be shaped and spaced apart to provide a reference measurement readable by user 2 (e.g., like tick marks), and at least one marker 37 may include a computer-readable code (e.g., a QR code) that is readable by imaging element 40 to determine characteristics fiber 36, allowing for automated and/or manual determinations of scale. For example, image analyzer 66 may determine the diameter of fiber 36 from the QR code, and automatically determine the scale therefrom, as described above. Establishing step 230 may be performed once within method 200 (e.g., ex vivo, in the factory or in the operating room), or repeatedly (in vivo, during a procedure, whenever imaging element 40 is moved).

Figure 3A:
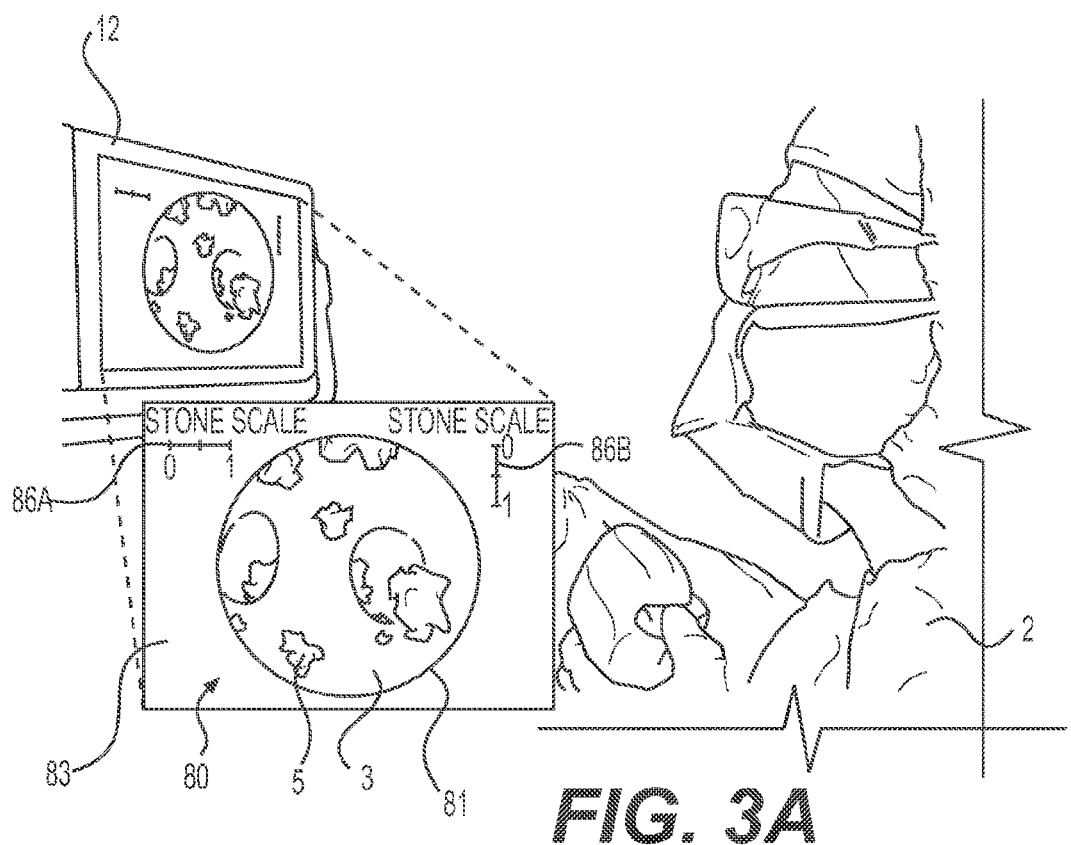
FIGS. 3A-D depict aspects of a visual representation generated from image data, and methods of using the system with the visual representation.
Figure 3B:
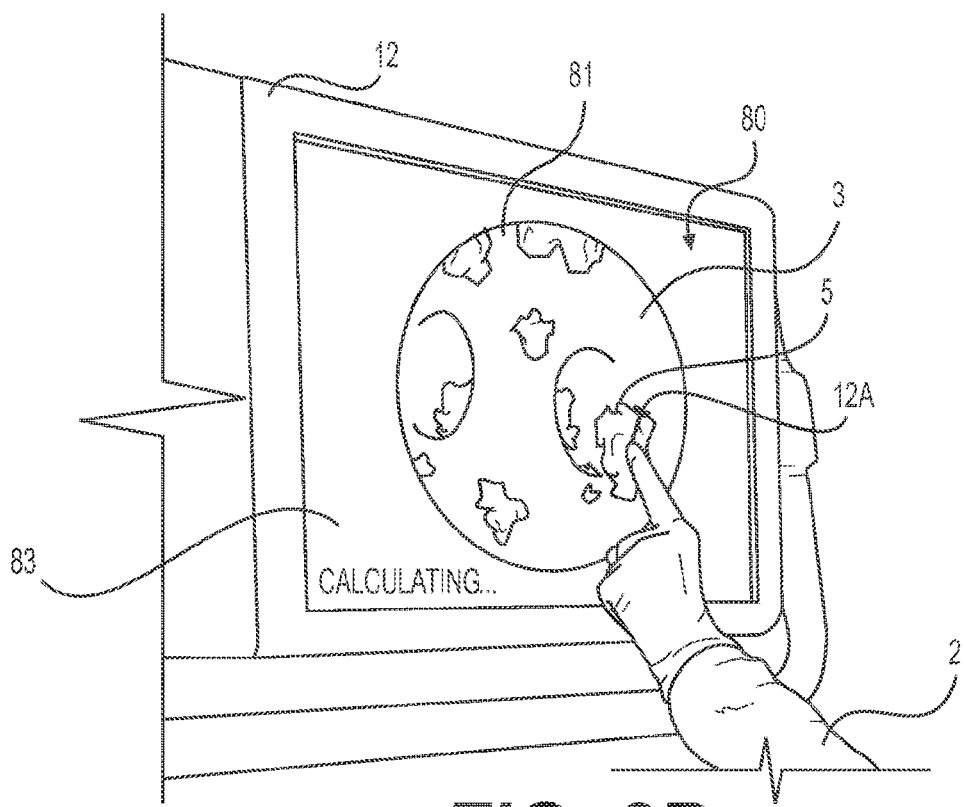
Figure 3C:
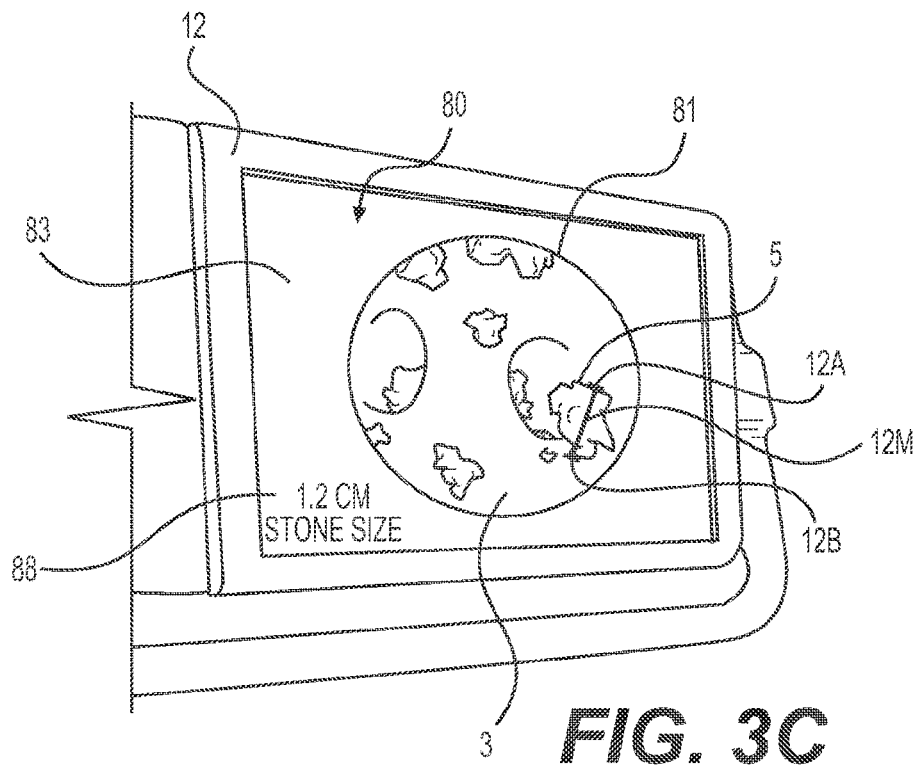

Sizing step 240 may include any intermediate steps for determining a two- or three-dimensional size of stone object 5. Numerous automated and manual aspects of sizing step 240 are now described. Manual aspects of step 240 are shown in FIGS. 3B-C, wherein a two-dimensional size of stone object 5 includes a stone width determined by: establishing a first reference point 12A on stone object 5 depicted in visual representation 80; establishing one or more second reference points 12B on stone object 5; and determining a reference measurement 12M between points 12A and 12B. Reference points 12A and 12B of FIGS. 3B-C may be established manually by user 2, for example, by touching various points on visual representation 80. Automated aspects of step 240 are also contemplated. For example, image analyzer 66 may be configured to automatically identify an external boundary of a stone object 5, locate points 12A and 12B on the external boundary, and determine reference measurement 12M therebetween.

However determined, manually or automatically, processing unit 60 may receive the reference measurement 12M between each reference point 12A and 12B (e.g., FIG. 3B); and determine the stone width by applying the scale to the reference measurement 12M (e.g., FIG. 3C). As described below, processing unit 60 may output an indicator of the stone width to indicator layer 83. Other two-dimensional sizes of stone object 5 may be determined in a like manner. For example, sizing step 240 may comprise determining a cross-sectional stone area; a maximum stone diameter or width; a minimum stone diameter or width; and/or the average stone diameter or width. Processing unit 60 may output an indicator for each of these sizes.

A three-dimensional size of stone object 5 may be determined in sizing step 240 by tracking characteristics of stone object 5 on a frame by frame basis. For example, as noted above, transmitting step 210 may include moving imaging element 40 to generate image data at different positions relative to stone object 5. Accordingly, sizing step 240 may comprise: determining a two-dimensional size of stone object 5 at each different position, and determining a three-dimensional size of object 5 based on the two-dimensional sizes. For example, sizing step 240 may comprise: determining a first size (e.g., a cross-sectional stone area) of stone object 5 in a first image frame; determining a second size (e.g., a stone width) of stone object 5 in a second image frame arranged transversely with the first imaging frame; and determining a three-dimensional size (e.g., a stone volume) for object 5 based on the first and second sizes (e.g., as a product of the cross-sectional stone area multiplied by the stone width). Other three-dimensional sizes (e.g., a surface area) may be determined using similar techniques. An indicator of each size may be output to indicator layer 83, as before.

Sizing step 240 (or transmitting step 210) also may comprise moving stone object 5. For example, step 240 may comprise: determining a first size (e.g., a cross-sectional stone area) of stone object 5 in a first position; moving stone object 5 to a second position; determining a second size (e.g., a stone width) of stone object 5 in the second position; and determining a three-dimensional size (e.g., a stone volume) for object 5 based on the first and second sizes (e.g., as a product of the cross-sectional stone area multiplied by the stone width). The distal end 36D of optical fiber 36 may be used to move stone object 5. For example, distal end 36D may rotate stone object 5 differently in each of the first and second positions.

In some aspects, sizing step 240 includes a treatment step. For example, sizing step 240 may comprise: determining a first size (e.g., a cross-sectional stone area) of stone object 5 in a first condition; applying a treatment energy configured to place stone object 5 into a second condition; determining a second size (e.g., a stone width) of stone object 5 in the second condition; and/or determining a three-dimensional size (e.g., a stone volume) for object 5 based on the first and second sizes (e.g., as a product of the cross-sectional stone area multiplied by the stone width). The treatment energy may be laser energy that is discharged from distal end 36D of fiber 36 to break stone object 5 into a plurality of stone fragments, each of which may move (e.g., revolve) relative to the next. Aspects of sizing step 240 may be used to track and size each stone fragment frame-by-frame within the video feed.

Comparing step 250 may include any intermediate steps for determining the removal status of stone object 5. For example, step 250 may comprise: comparing, with processing unit 60, a size of stone object 5 (e.g., a maximum stone width) with a predetermined maximum size (e.g., a maximum width of working channel 34, a maximum capture width of a retrieval basket extendable therefrom, and/or a maximum width of a ureter or an access sheath). The predetermined maximum size may be relative to a maximum post-treatment width of stone object 5 so that the removal status may be utilized to determine whether object 5 need be further treated and/or removed. Once determined, an indicator of the removal status also may be output to indicator layer 83. Any number of removal statuses may be determined in this manner. For example, comparing step 250 may comprise: determining a first removal status if the size of stone object 5 is greater than the predetermined maximum width (e.g., greater than 2 mm), and determining a second removal status if the size of stone object 5 is less than said maximum width (e.g., less than 2 mm).

Figure 3D:
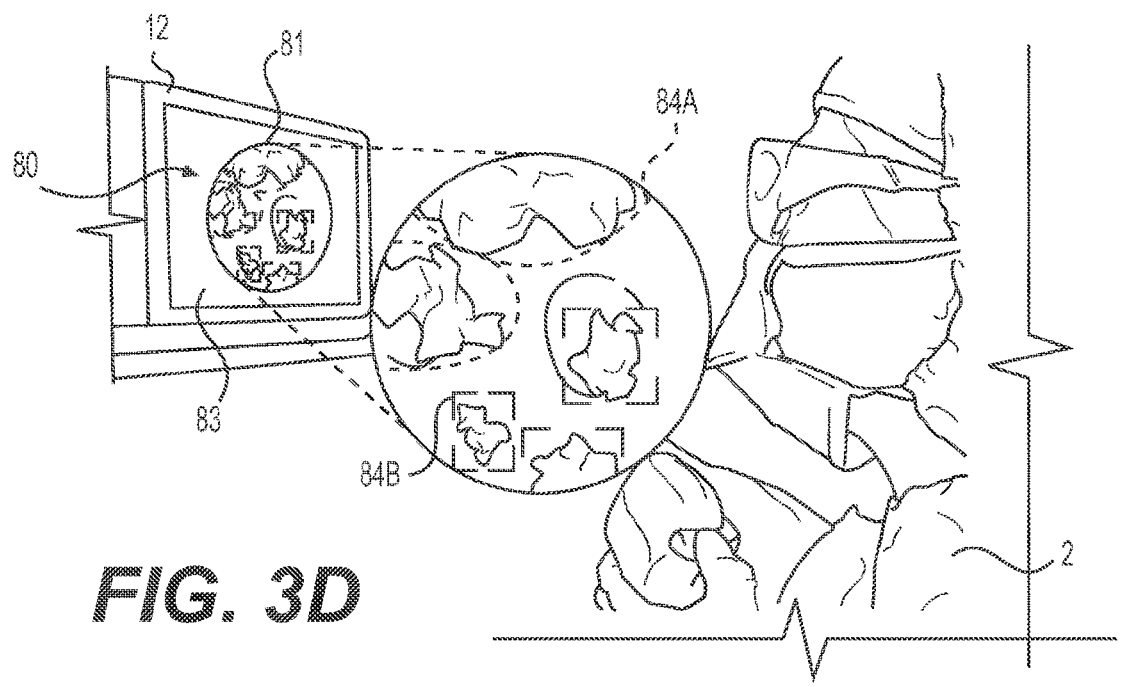

Augmenting step 260 may include any intermediate steps for providing visual representation 80 with at least one indicator responsive to a characteristic of stone object 5. Numerous indicators have been described herein. For example, augmenting step 260 may comprise: overlaying portions of indicator layer 83 onto portions of image data layer 81. The overlaid portions of indicator layer 83 may include any of the indicators described above. For example, as shown in FIG. 3D, augmenting step 260 may comprise: overlaying a first removal status indicator 84A (shown, for example, as a circular dotted line of any color) over any stone object 5 associated with the first removal status, and a second removal status indicator 84B (shown, for example, as a square dotted line of another color) over any stone object 5 associated with the second removal status.

Once augmented in step 260, visual representation 80 and/or other notification technologies may be used to alert user 2 regarding the removal status of stone object 5. For example, if a plurality of stone objects 5 are depicted in visual representation 80, then augmenting step 280 may comprise highlighting, in visual representation 80 (e.g., FIG. 3D), any stone objects 5 that cannot be removed (e.g., those with first status indicator 84A in FIG. 3D), and/or highlighting any stone objects 5 that are ready for removal (e.g., those with second status indicator 84B in FIG. 2D). Audible alerts may also be provided by a sound generating technology responsive to control signals from processor 60, such as a speaker mounted on handle 20.

Visual representation 80 may be further augmented in step 260 to include indicators responsive to the scale and/or sizes described above. For example, as shown in FIG. 3A, indicator layer 83 may include a first stone scale indicator 86A aligned with a first axis, and a second stone scale indicator 86B aligned with a second axis. As shown in FIG. 3C, a size indicator 88 responsive to size 84 also may be included in indicator layer 83. Any of these indicators may be included in visual representation 80 by, for example, combining image data layer 81 with indicator layer 83.

As described above, imaging element 40 may be moved relative to each of the one or more stone objects 5 to enhance the imaging data. Method 200 may be further modified to leverage these movements. For example, method 200 may comprise: identifying a reference identifier for stone object 5 (an identifying step 280); associating the reference identifier with characteristics of the object 5 (an associating step 282); tracking the characteristics during a procedure (a tracking step 284); and/or further augmenting visual representation 80 responsive to the characteristics (a further augmenting step 286). The reference identifier may be a fingerprint for each stone object 5 that is determined, with image analyzer 66, based on unique physical characteristics of object 5. An exemplary fingerprint may be based upon any aspect of the two- or three-dimensional sizes described herein.

Associating step 282 may comprise: linking each reference identifier with characteristics stone object 5. The linked characteristic may include any two or three-dimensional size described herein, as well as any other information specific to stone object 5. Step 282 may be performed on a frame by frame basis whenever the fingerprint of stone object 5 is identified in step 280, even if the location of imaging element 40 is unknown. For example, identifying step 280 may be automatically performed by image analyzer 66 whenever stone object 5 is moved into view of imaging circuits 42, allowing user 2 to move imaging element 40 freely within body cavity 3.

Tracking step 284 may be used to continuously update visual representation 80. For example, tracking step 284 may comprise: identifying a first or initial size of stone object 5; determining a second or subsequent size of the object 5; and calculating a difference between the first and second sizes. If a difference of sufficient magnitude is detected (e.g., +/−5%), then further augmenting step 286 may comprise: updating indicator layer 83 to account for the difference; and updating the removal status of stone object 5.

Figure 4:
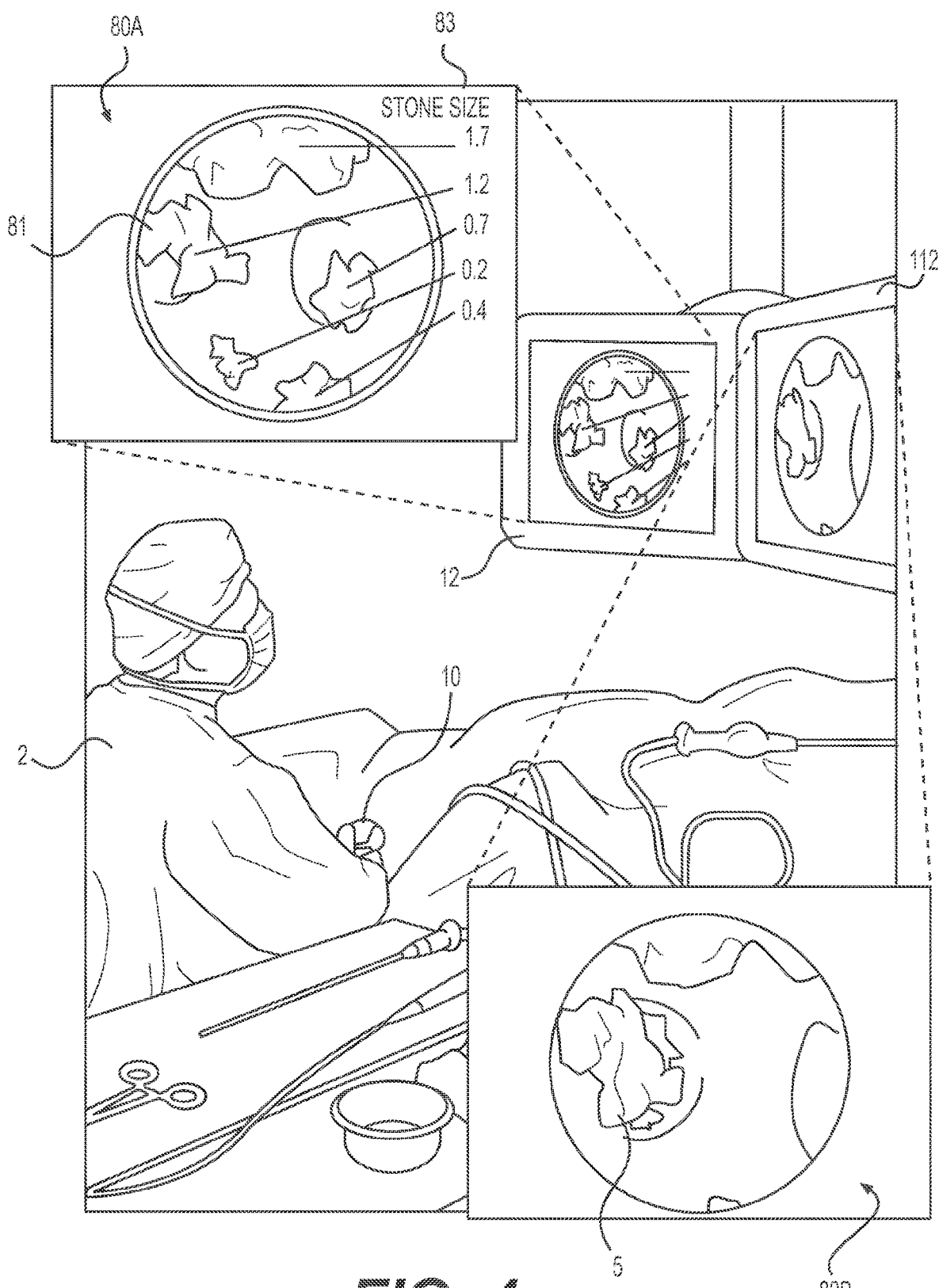
FIG. 4 depicts additional aspects of a visual representation generated from image data, and methods of using the system with the visual representation.

Aspects of method 200 have been described with reference to a single stone object 5; however, as shown in FIG. 4, the two- or three-dimensional size of a plurality of stone objects 5 may likewise be determined. Processing unit 60 may be configured to simultaneously determine characteristics for each of the plurality of stone objects 5 frame by frame. For example, image analyzer 66 may be configured to: identify each of the plurality of stone objects 5 within a first image frame; sequentially determine a size of each object 5 in the first frame using any method described herein; and track the determined sizes in one more second frames. Second actuator 24, for example, may be used to initiate or advance the sequence. Indicator layer 83 may include an indicator responsive to the size of each stone object 5, as in FIG. 4, wherein each indicator is depicted as a measurement with a call-out.

Aspects of system 100 and method 200 have also been described with reference to one or more interface devices 12. Any number of interface devices 12 may be used. For example, as shown in FIG. 4, an augmented version 80A of visual representation 80 may be depicted by a first interface device 12, while an unaugmented version 80B of representation 80 is simultaneously depicted on a second interface device 112. This configuration allows user 2 to, for example, zoom display device 12 out to determine the size of a plurality of stone objects 5, and/or independently zoom display device 112 in to treat a particular stone object 5.

Numerous means for determining a stone depth for stone object 5 have been described above, including moving imaging element 40 and/or moving object 5. Alternate means are contemplated. For example, digital camera circuit 42 may be capable of focusing upon stone object 5, allowing stone depth to be determined relative to a focal length. Camera circuit 42 may alternatively include a plurality of cameras, allowing stone depth to be determined from binocular cues. Alternatively still, imaging element 40 may include a wave energy transducer 46 configured to generate wave energy images of body cavity 3 and/or stone object 5. Any type of wave energy can be used, including light or sound. As shown in FIG. 1B, for example, element 40 may include a transducer 46 (e.g., laser source or ultrasound transducer) configured to: direct a wave energy toward stone object 5; receive a reflected portion of the wave energy; and generate wave energy images from the reflected portion of wave energy. The resulting wave energy images may be output to processing unit 60 with transceiver 46 and used to aid in determining any of the two- and three-dimensional sizes described herein, including stone depth.

Aspects of method 200 may be modified for use with transducer 46. For example, sizing step 240 may comprise: directing, with processing unit 60, a wave energy from the wave energy transducer 46 toward a stone object 5; receiving, with transducer 46, a reflected portion of the wave energy; defining from the reflected portion of the wave energy, with the processing unit 60, a stone depth of stone object 5 in a direction transverse with an imaging plane of the image data; and determining the stone volume of object 5 based on the depth. According to some aspects, an average stone depth of stone object 5 may be determined responsive to a wave energy shadow created by stone object 5, and then multiplied with a cross-sectional stone area from step 240 to determine the stone volume. Because of transducer 46, the average stone depth may be determined without moving imaging element 40. Similar techniques may be utilized to determine a surface area and/or density of stone object 5; or to verify any two or three-dimensional size determined without the aid of transducer 46. As before, an indicator for these sizes may be output to indicator layer 83.

As shown in FIG. 1B, imaging element 40 may optionally include a locator device 50 configured to output a location signal to processing unit 60. For example, the location signal may be generated by locator device 50 whenever image data is generated by imaging element 40. Any known technology may be included within locator device 50 and utilized to generate the location signal, include magnetic and/or ultrasound-based technologies.

Method 200 may be modified for use with locator device 50. For example, identifying step 280 may include locating imaging element 40 from the location signal, with processing unit 60, in a body information model generated according to the exemplary systems and methods described in U.S. Provisional Patent Application No. 62/420,981, filed Nov. 11, 2016, the entirety of which is incorporated by reference herein. In this example, the reference identifier for each stone object 5 may include a reference location for each stone object 5 within the body information model, such that identifying step 280 comprises locating each stone object 5 within the body information model; and associating step 282 comprises linking each reference location with characteristics of stone object 5. Tracking step 284 may be further configured to track the location of device 50 relative to each reference location, allowing visual representation 80 to be generated and augmented responsive to the movements of imaging element 40 within body cavity 3.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents all fall in the scope of the aspects described herein. Accordingly, the present disclosure is not to be considered as limited by the foregoing description.

The invention claimed is:

1. A processing unit for a medical imaging system, comprising:
    a transceiver to couple to an imaging element of an endoscope;
    a processor coupled to the transceiver; and
    a memory coupled to the processor, the memory comprising instructions stored thereon, which when executed by the processor cause the processing unit to:

receive, from the imaging element via the transceiver, a plurality of image frames;

identifying at least one stone object from a first image frame of the plurality of image frames;

determining a first two-dimensional (2D) size for the at least one stone object based in part on the first image frame;

identifying the at least one stone object from a second image frame of the plurality of image frames;

determining a second 2D size for the at least one stone object based in part on the second image frame; and determining a three-dimensional (3D) size for the at least one stone object based in part on first 2D size and the second 2D size, wherein the at least one stone object is depicted from different angles each of the first image frame and the second image frame.

2. The processing unit of claim 1, the instructions, when executed by the processor cause the processing unit to generate a visual representation comprising an indication of the 3D size of the at least one stone object.

3. The processing unit of claim 2, wherein the visual representation comprises an image frame of the plurality of image frames.

4. The processing unit of claim 3, the instructions, when executed by the processor cause the processing unit to:
compare the size of the at least one stone object with a predetermined size to determine a removal status; and
augment the visual representation to include an indicator of the removal status.

5. The processing unit of claim 4, wherein the indicator of the removal status is a geometric shape overlaid over the at least one stone object in the visual representation.

6. The processing unit of claim 2, the instructions, when executed by the processor cause the processing unit to transmit the visual representation to an interface device for display.

7. A medical imaging system, comprising:
an interface device; and
a processing unit, the processing unit comprising:
a transceiver to couple to an imaging element of an endoscope;
a processor coupled to the transceiver; and
a memory coupled to the processor, the memory comprising instructions stored thereon, which when executed by the processor cause the processing unit to:
receive, from the imaging element via the transceiver, a plurality of image frames;
identifying at least one stone object from a first image frame of the plurality of image frames;
determining a first two-dimensional (2D) size for the at least one stone object based in part on the first image frame;
identifying the at least one stone object from a second image frame of the plurality of image frames;
determining a second 2D size for the at least one stone object based in part on the second image frame; and
determining a three-dimensional (3D) size for the at least one stone object based in part on first 2D size and the second 2D size,
wherein the at least one stone object is depicted from different angles each of the first image frame and the second image frame.

8. The system of claim 7, the instructions, when executed by the processor cause the processing unit to generate a visual representation comprising an indication of the 3D size of the at least one stone object.

9. The system of claim 8, the instructions, when executed by the processor cause the processing unit to transmit the visual representation to the interface device for display.

10. The system of claim 9, wherein the visual representation comprises an image frame of the plurality of image frames.

11. The system of claim 10, the instructions, when executed by the processor cause the processing unit to:
compare the size of the at least one stone object with a predetermined size to determine a removal status; and
augment the visual representation to include an indicator of the removal status.

12. The system of claim 11, wherein the indicator of the removal status is a geometric shape overlaid over the at least one stone object in the visual representation.

13. The system of claim 7, wherein the interface device is a touchscreen display.

14. The system of claim 7, comprising the endoscope, wherein the endoscope is a ureteroscope.

15. At least one non-transitory computer readable storage medium comprising instructions, which when executed by a processing unit of a medical imaging system cause the processing unit to:
receive, from an imaging element of an endoscope via a transceiver coupled to the processing unit, a plurality of image frames;
identifying at least one stone object from a first image frame of the plurality of image frames;
determining a first two-dimensional (2D) size for the at least one stone object based in part on the first image frame;
identifying the at least one stone object from a second image frame of the plurality of image frames;
determining a second 2D size for the at least one stone object based in part on the second image frame; and
determining a three-dimensional (3D) size for the at least one stone object based in part on first 2D size and the second 2D size, wherein the at least one stone object is depicted from different angles each of the first image frame and the second image frame.

16. The at least one non-transitory computer readable storage medium of claim 15, the instructions when executed by the processing unit cause the processing unit to generate a visual representation comprising an indication of the 3D size of the at least one stone object.

17. The at least one non-transitory computer readable storage medium of claim 16, wherein the visual representation comprises an image frame of the plurality of image frames.

18. The at least one non-transitory computer readable storage medium of claim 17, the instructions, when executed by the processor cause the processing unit to:
compare the size of the at least one stone object with a predetermined size to determine a removal status; and
augment the visual representation to include an indicator of the removal status.

19. The at least one non-transitory computer readable storage medium of claim 18, wherein the indicator of the removal status is a geometric shape overlaid over the at least one stone object in the visual representation.

20. The at least one non-transitory computer readable storage medium of claim 17, the instructions, when executed by the processor cause the processing unit to transmit the visual representation to an interface device for display.

\* \* \* \* \*